United States Patent
Tam et al.

(10) Patent No.: US 9,254,181 B2
(45) Date of Patent: Feb. 9, 2016

(54) AUTOMATIC SURGICAL LIGHTING DEVICE AND ITS LIGHTING METHOD

(71) Applicant: Tam Weng-Heng, Ho Man Tin, Kowloon (HK)

(72) Inventors: Weng-Heng Tam, Kowloon (HK); Weng-Kong Tam, Kowloon (HK)

(73) Assignee: Tam Weng Heng, Kowloon (HK)

( * ) Notice: Subject to any disclaimer, the term of this patent is extended or adjusted under 35 U.S.C. 154(b) by 487 days.

(21) Appl. No.: 13/724,970

(22) Filed: Dec. 21, 2012

(65) Prior Publication Data

US 2014/0015948 A1  Jan. 16, 2014

(30) Foreign Application Priority Data

Jul. 11, 2012  (CN) .......................... 2012 1 0240347

(51) Int. Cl.
 *A61B 19/00* (2006.01)
(52) U.S. Cl.
 CPC .................................. *A61B 19/5202* (2013.01)
(58) Field of Classification Search
 CPC ................................................... A61B 19/5202
 USPC ........................................................... 348/77
 See application file for complete search history.

(56) References Cited

U.S. PATENT DOCUMENTS

| | | | |
|---|---|---|---|
| 6,299,307 B1 * | 10/2001 | Oltean et al. | 351/210 |
| 7,567,833 B2 * | 7/2009 | Moctezuma De La Barrera et al. | 600/424 |
| 2005/0174473 A1 * | 8/2005 | Morgan et al. | 348/370 |
| 2013/0113909 A1 * | 5/2013 | DeLand | 348/77 |

FOREIGN PATENT DOCUMENTS

| | | |
|---|---|---|
| CN | 2233722 Y | 8/1996 |
| CN | 1164381 A | 11/1997 |
| CN | 2458983 Y | 11/2001 |
| JP | 2004129978 | 4/2004 |

* cited by examiner

*Primary Examiner* — Behrooz Senfi
(74) *Attorney, Agent, or Firm* — Muncy, Geissler, Olds & Lowe, P.C.

(57) ABSTRACT

The present invention provides an automatic surgical lighting device and its lighting method. The surgical lighting device is located to face a target area and includes a supporting element that is connected to at least a moving element that is above the target area. A lighting capture module set on the moving element is used to illuminate the target area and capture the image of the target area in order to send feedback signal. Both the lighting capture module and moving element are electronically connected to at least one control unit. The control unit, base on the feedback signal received, moves the lighting capture module via the moving element till the whole image of the target area is obtained. By this method, the surgery quality is improved, the surgery time is shortened and the risk of cross infection and the consequent litigation is lowered.

13 Claims, 6 Drawing Sheets

AUTOMATIC SURGICAL LIGHTING DEVICE AND ITS LIGHTING METHOD

BACKGROUND

1. Field of the Invention

The present invention relates to a lighting method. More specifically, it relates to an automatic surgical lighting device and its lighting method.

2. Description of the Related Art

In the operation rooms of hospitals, the location to be operated on a patient is illuminated using surgical light. As shown in FIG. 1, many surgical lighting devices (10) are hanged, by means of several mechanic arms, on the ceiling, walls or frames inside of the hospital. These movable mechanical arms allow adjustment of the relative position of the surgical light to the patient. Usually, the surgical light is positioned behind the surgeon that the head of the surgeon is positioned between the surgical light and the operation spot. The quality of the surgical light affects deeply the result of the operation.

There are several important issues to be considered about the surgical light. First, the lighting field of the surgical light varies depending on the position of the patient. Usually, during the operation, the surgical light is above the heads of the medical staff that moves unsystematically and blocks the light. In the case of mouth surgical lighting, the upper, lower, left and right areas of the mouth all need to be in the lighting field and a single illuminating source can hardly light all part of the mouth. Thus, the position of the surgical light has to be changed constantly to allow perfect lighting of the target area. Furthermore, if the surgeon has to operate the surgical light manually, the cross infection among patients can occurred during operations. Moreover, it is bothersome for the surgeon to multitask. For example, when a dentist deals with hard tissue such as teeth, the shadowed spot of the teeth cannot be seen even with the lighting and the quality of the operation is affected.

Therefore, the present invention provides an automatic surgical lighting device and its method to solve the above-mentioned issues and the known problems.

SUMMARY

The main purpose of the present invention is to provide an automatic surgical lighting device and its lighting method. A lighting capture module is used to capture the image of the target area and, according to the feedback signal; the lighting angle is changed constantly until the whole target area is captured. By this method, the lighting quality and the surgery quality are improved, the surgery time is shortened and the risk of cross infection and the consequent litigation is lowered.

To achieve the above-mentioned purpose, the present invention provides an automatic surgical lighting device facing the target area. The said automatic surgical lighting device comprises a supporting element that is connected to at lease one moving element that is positioned above the target area. A central pivot, with its axis vertical to the target area, connects the supporting element and moving element. At least one lighting capture module is set on the moving element to light the target area, capture the image of the target area constantly and send according feedback signal. At least one control unit is electronically connected to the lighting capture module and the moving element for receiving the feedback signal that is used to move the lighting capture module via the moving element until the whole image of the target area is obtained.

The present invention also provides an automatic surgical lighting method that uses at least one lighting capture module that is set on at least one moving element. First, the lighting capture module illuminates the target area, capture the image of the target area and send an according feedback signal. Then, the feedback signal received is used to move the lighting capture module via the moving element until the whole image of the target area is obtained.

For further understanding and acknowledge of the structural characteristic and the effects of the present invention, the following preferred embodiments and figures are illustrated.

DETAILED DESCRIPTION

Figure 1:
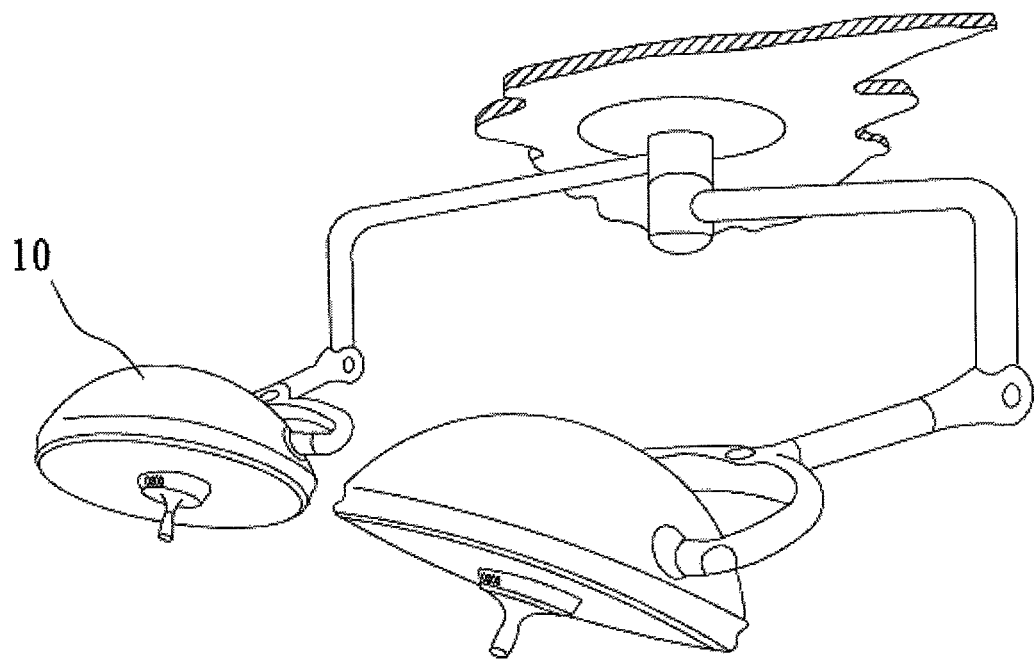
FIG. 1 is the schematic diagram of the surgical lighting device of prior art.

As shown in FIG. 2 to FIG. 5, the automatic surgical lighting device is positioned facing the target area (12). The target area (12) can be a mouth cavity area, a detectable target object in an operation, and hands of the surgeon, a dental hand-piece, a dental mirror, teeth or the shape of the mouth. Here, the mouth cavity area is used for illustration.

The present invention comprises a supporting element (14) that is a supporting set installed on the ceiling or a supporting frame attached to the dental chair. Here the supporting set is used for illustration. The supporting element (14) is connected to a mechanical arm (16) and the mechanical arm (16) is connected to a central pivot (18) to allow the mechanical arm (16) be placed between the supporting element (14) and the central pivot (18). The central pivot (18) is then connected to at least one moving element (20) and is situated between the moving element (20) and both the supporting element (14) and the mechanic arm (16). The axis of the central pivot (18) is vertical to the target area (12). In this preferred embodiment, several moving elements are used (e.g. 4) and they are situated above the target area (12). At least one lighting capture module (22) is set on the moving elements to illuminate the target area (12), capture constantly and periodically the image of the target area (12) and send according feedback signal. In this preferred embodiment, a lighting capture module (22) is set on each of the moving elements (20). At least one first shifting control unit (24) is set on the mechanic arm (16) and a second shifting control unit (26) is set on the central pivot (18) and the mechanic arm (16). The lighting capture module (22), the moving element (20), the first shifting control unit (24) and the second shifting control unit (26) are all electronically connected to at least one control unit (28). The control unit (28) can be set exteriorly or integrated in the lighting capture module (22) or supporting element (14). In this illustration, it is integrated in the supporting element (14).

The control unit (28) is preset with at least one target zone corresponding to at least one lighting capture module (22). The control unit (28) receives the feedback signal, compares with the template image of the corresponding target zone and moves the lighting capture module (22) via the moving element (20) according to the result obtained. At the same time, the control unit (28), based on the feedback signal, moves the mechanic arm (16) via the first shifting control unit (24) in order to move the lighting capture module (22) till the above-mentioned image is in the corresponding target zone and the image of the whole target area (12) is captured. Furthermore, based on the feedback signal, the control unit (28), via the second shifting control unit (26), also makes the central pivot (18) pivot around its conjunction with the mechanic arm (16) and keeps the central pivot (18) remain vertical to the target area (12).

Figure 3:
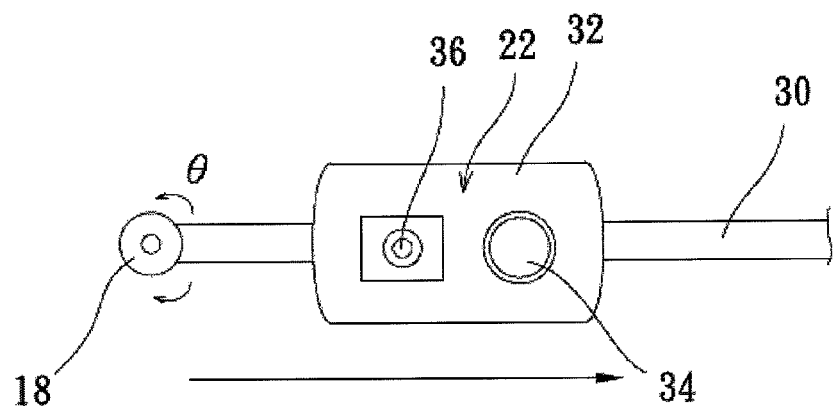
FIG. 3 is the schematic diagram of rotation of the lighting capture module on the axis of the central pivot.
Figure 4:
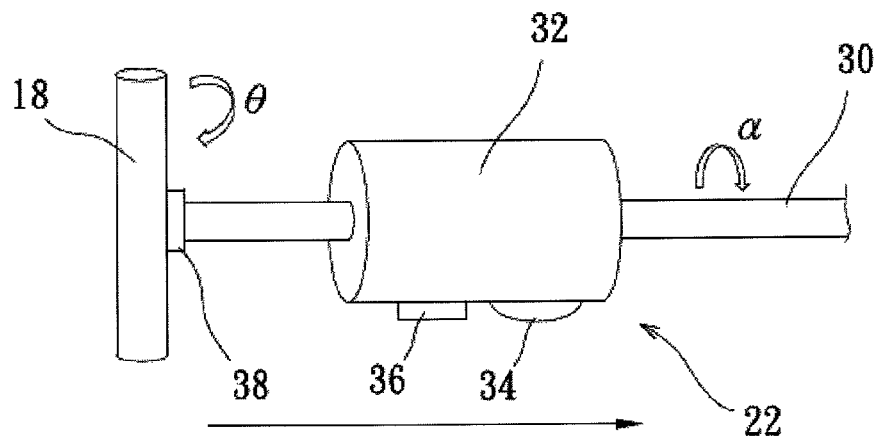
FIG. 4 is the schematic diagram of rotation of the lighting capture module on the axis of the sliding bar.
Figure 5:
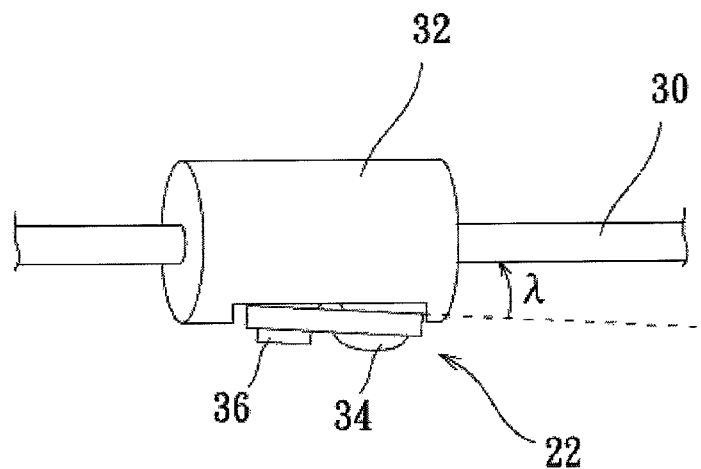
FIG. 5. is the schematic diagram of rotation of the lighting capture module on the axis direction vertical to the sliding bar.

Each moving element (20) further comprises a sliding bar (30) and a third shifting control unit (32). The sliding bar (30) is connected to the central pivot (18) and is situated above the target area (12). The third shifting control unit (32) is set on the sliding bar (30) and is electronically connected to control unit (28). The control unit (28) receives the feedback signal, compares with the template image of the corresponding target zone and, based on the result, moves the lighting capture module (22) on the sliding bar (30) using the third shifting control unit (32) till the image is in the corresponding target zone and the whole image of the target area (12) is obtained. As shown in FIG. 3, the control unit (28), based on the feedback signal, moves the lighting capture module (22) on the sliding bar (30) using the third shifting control unit (32). As shown in FIG. 4, the control unit (28), based on the feedback signal, makes the lighting capture module (22) rotate by angle a on the axis direction of the sliding bar (30) using the third shifting control unit (32). As shown in FIG. 5, the control unit (28), based on the feedback signal, makes the lighting capture module (22) rotate by angle λ vertical to the axis direction of the sliding bar (30) using the third shifting control unit (32).

Each lighting capture module (22) further comprises an illuminating source (34) and an image detector (36). The illuminating source (34) is set on the sliding bar (30) via the third shifting control unit (32) and lights the target area (12). The image detector (36) is set on the sliding bar (30) via the third shifting control unit (32) and connects electronically to the control unit (28). The image detector (36) capture constantly and periodically the image of the target area (12) in order to send feedback signals.

At least one fourth shifting control unit (38) is set on the central pivot (18) and the sliding bar (30). Because there are several sliding bars (30), there are several fourth shifting control units (38) situated between each sliding bar (30) and central pivot (18). The fourth shifting control units (38) are electronically connected to the control unit (28) that receives feedback signals in order to compare with the above-mentioned image of the corresponding target zone. And, according to the result obtained, the fourth shifting control unit (38) makes the sliding bar (30) rotate on the axis direction of the central pivot (18) in order to move the lighting capture module (22) to make the image situate in the corresponding target zone and that the whole image of the target area (12) is obtained. As shown in FIG. 3 and FIG. 4, the rotate angle is θ.

Figure 2:
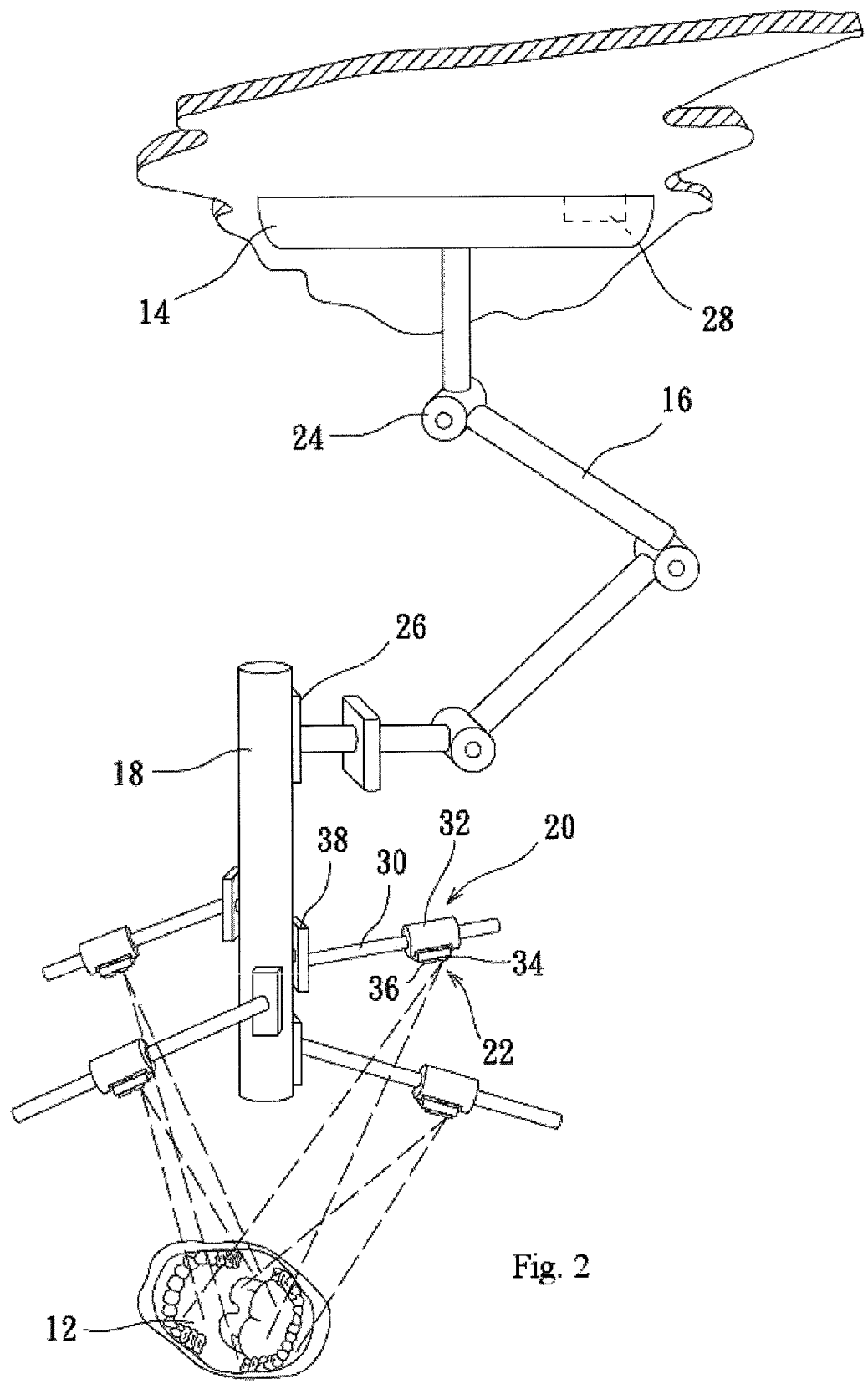
FIG. 2 is the structure diagram of the present invention with several moving elements.
Figure 6:
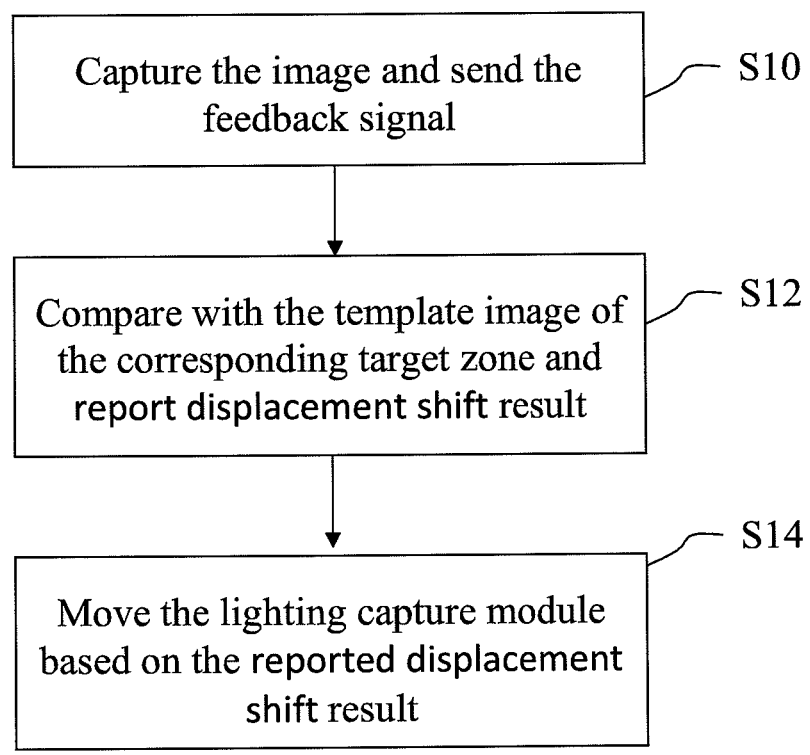
FIG. 6. is the flowchart of the present invention.

Please refer to FIG. 2 and FIG. 6 at the same time. The lighting method of the present invention is as follows. First, the full image of target area (12) is preset in the control unit (28). The full image consists of at least one target zone of the lighting capture module (22). There are thus several target zones, for example, four. Then, as shown in step S10, the illuminating source (34) and the image detector (36) are turned on, where in the illuminating source (34) emits light randomly and the image detector (36) captures the image of the target area (12) randomly, constantly and periodically to send corresponding feedback signals. Then, as shown in step S12, the control unit (28), upon receiving the feedback signal for comparing with the captured image of the corresponding target zone, reports displacement shift result. Finally, as shown in step S14, the control unit (28), based on the reported displacement shift result, moves the mechanic arm (16) via the first shifting control unit (24), makes the lighting capture module (22) slide or rotate on the sliding bar (30) via the third shifting control unit (32), and makes the sliding bar (30) rotate on the axis direction of central pivot (18) via the fourth shifting control unit (38) to move the lighting capture module (22) in order to make the image be with in the corresponding target zone and the whole image of the target area (12) be captured. Since the illuminating source (34) is almost at the same position with the image detector (36), the illuminating source (34) can illuminate the whole target area (12). Furthermore, the control unit (28), based on the reported displacement shift result obtained, rotates the central pivot (18) on the axis of its conjuncture with the mechanic arm (16) via the second shifting control (26) in order to have the axis of the central pivot (18) vertical to the target area (12). By means of control via the first shifting control unit (24), the second shifting control unit (26), the third shifting control unit (32) and the fourth shifting control unit (38), the lighting angle can be adjusted constantly and improve the quality of lighting and the operation. Since the target area (12) is not shadowed, the operation view is fine and the operation time can be shortened. Moreover, the automatic lighting device in the present inventions is automatic instead of manual and thus lowers the risk of cross-infection and possible litigations.

The step S12 and step S14 can be replace by a single step, i.e., after the step S10, the control unit (28) receives the feedback signal and moves the lighting capture module (22) via the moving element (20) till the image is situated in the corresponding target zone and the full image of the target area (12) is obtained.

Figure 7:
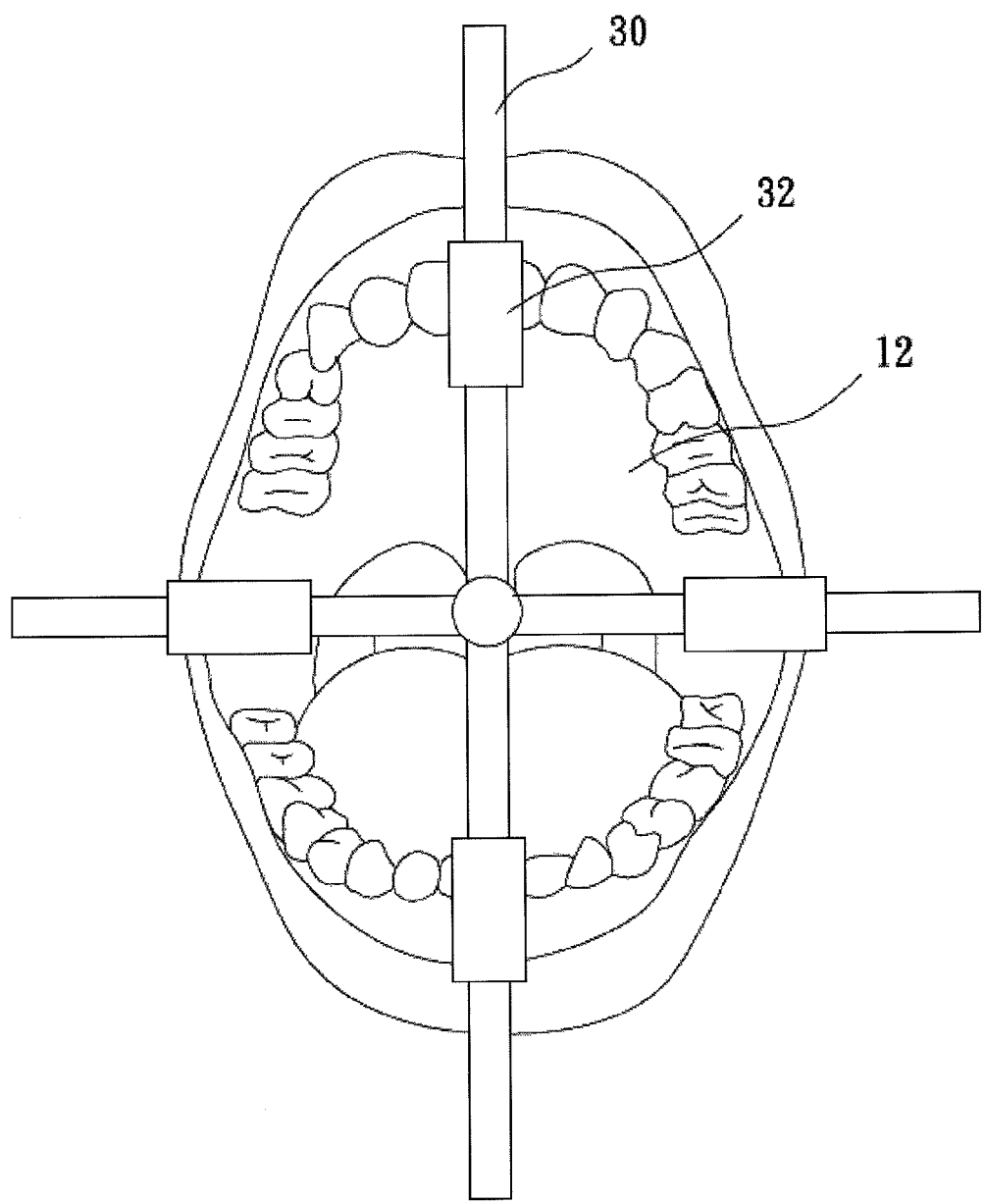
FIG. 7 is the schematic diagram of the angle partitions for the rotation of sliding bar.

As shown in FIG. 7, to avoid the sliding bars (30) colliding one another when the sliding bars (30) rotates on the axis direction of the central pivot (18), the control unit divides the 360 degree into several angle partitions and, based on the feedback signal, makes each sliding bar (30) rotate within its partition on the axis direction of the central pivot (18) via the fourth shifting control unit (38).

Figure 8:
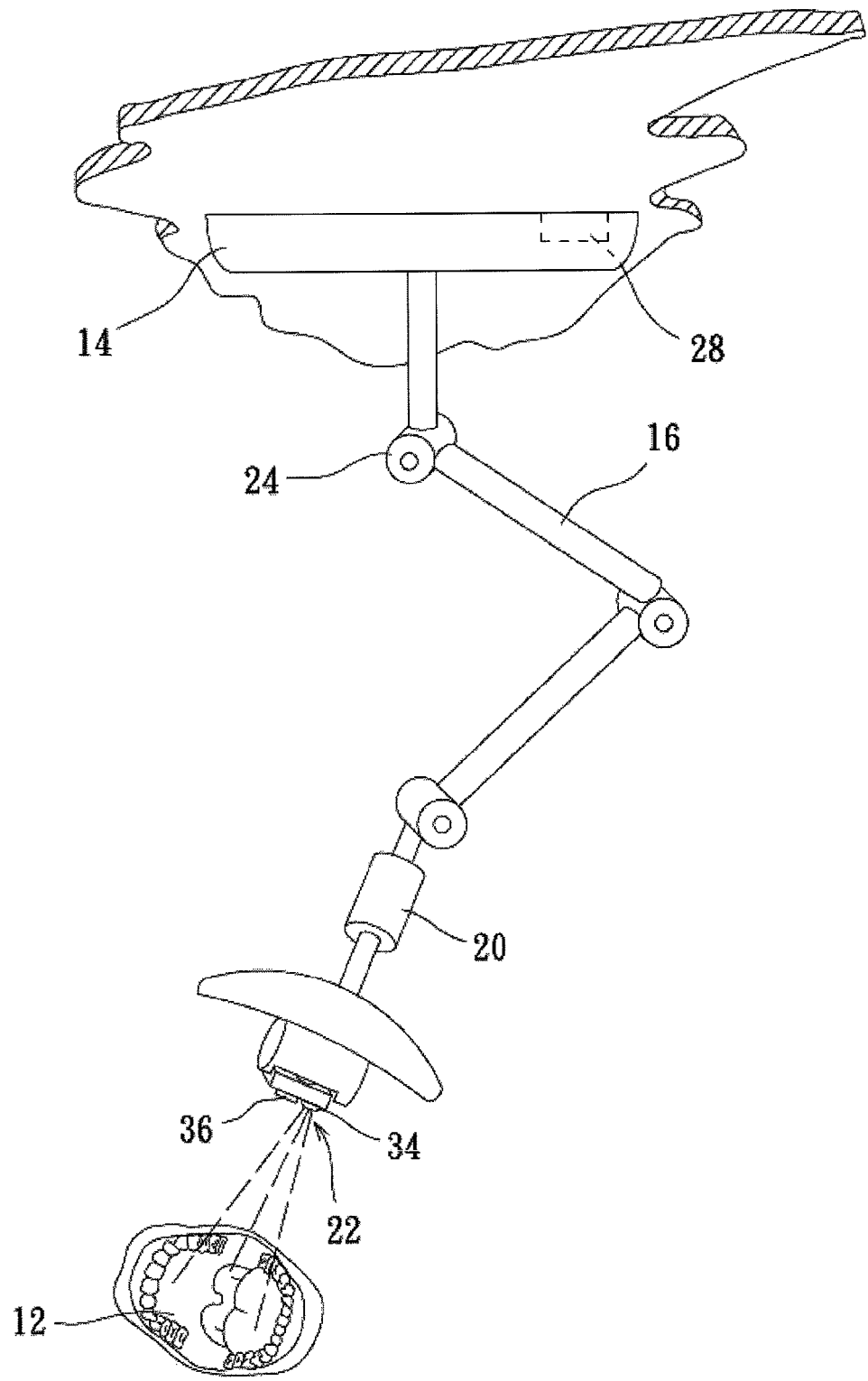
FIG. 8 is the schematic diagram of the present invention with a moving element.

As shown in FIG. 8, here a moving element (20) is used in the preferred embodiment. The present invention comprises a supporting element (14) which is a supporting frame installed on the ceiling. The supporting element (14) connects to a mechanic arm (16) that is connected to a moving element (20) and is situated between the supporting element (14) and the moving element (20). A lighting capture module (22) is installed on the moving element (20) to light the target area (12) and capture the image of target area (12) constantly and periodically in order to send corresponding feedback signal. At least one first shifting control unit (24) is set on the mechanic arm (16). The lighting capture module (22), the moving element (20) and the first shifting control unit (24) are all electronically connected to at least one control unit (28). The control unit (28) can be set exteriorly or integrated in the lighting capture module (22) or supporting element (14). In this illustration, it is integrated in the supporting element (14). The control unit (28) is preset with at least one target zone corresponding to at least one lighting capture module (22). The control unit (28) receives the feedback signal, compares with the template image of the corresponding target zone and moves the lighting capture module (22) via the moving element (20) according to the result obtained. At the same time, the control unit (28), based on the feedback signal, moves the mechanic arm (16) via the first shifting control unit (24) in order to move the lighting capture module (22) till the above-mentioned image is in the corresponding target zone and the image of the whole target area (12) is captured. Besides, the components of the lighting capture module (22) are identical to the earlier description.

Please refer to FIG. 6 and FIG. 8 at the same time. The lighting method of the present invention is as follows. First, the full image of target area (12) is preset in the control unit (28). The full image consists of at least one target zone of the lighting capture module (22). Then, as shown in step S10, the illuminating source (34) and the image detector (36) are turned on, where in the illuminating source (34) emits light randomly and the image detector (36) captures the image of the target area (12) randomly, constantly and periodically to send corresponding feedback signals. Then, as shown in step S12, the control unit (28), upon receiving the feedback signal for comparing with the captured image of the corresponding target zone, reports displacement shift result. Finally, as shown in step S14, the control unit (28), based on the reported displacement shift result, moves the lighting capture module (22) via the moving element (20) and also moves the mechanic arm (16) via the first shifting control unit (24) to move the lighting capture module (22) in order to make the image be with in the corresponding target zone and the whole image of the target area (12) be captured. Since the illuminating source (34) is almost at the same position with the image detector (36), the illuminating source (34) can illuminate the whole target area (12).

Similarly, the step S12 and step 514 can be replace by a single step, i.e., after the step S10, the control unit (28) receives the feedback signal and moves the lighting capture module (22) via the moving element (20) till the image is situated in the corresponding target zone and the full image of the target area (12) is obtained.

To sum up, the present invention can change the lighting angle automatically to improve the surgical lighting quality, shorten the operation time and lower the risk of cross-infection.

The preferred embodiments illustrated are set for facilitating the reader and not for limiting the scope of the present invention. All changes and modifications on the shape, structure, characteristic or spirit based on the present invention are in the scope of what is claimed in the patent application of the present invention.

What is claimed is:

1. An automatic surgical lighting device facing the target area, said automatic surgical lighting device comprises:
    a supporting element;
    a plurality of moving element that is connected to the supporting element;
    a plurality of lighting capture module is set on the moving elements to light the target area, capture the image of the target area and send according feedback signal;
    at least one control unit that is electronically connected to the lighting capture module and the moving element for receiving the feedback signal;
    a central pivot, with its axis vertical to the target area, that is between the supporting element and moving element and connects them;
    wherein each the moving element comprises:
    a sliding bar that is connected to the central pivot and is situated above the target area;
    a third shifting control unit set on the sliding bar and electronically connected to the control unit;
    a plurality of fourth shifting control units which are set on the central pivot and the sliding bar and are electronically connected to at least one control unit, each lighting capture module is set on each sliding bars via each third shifting control unit, at least one control unit divides the 360 degree into several angle partitions and, based on the feedback signal, makes each sliding bar rotate within its partition on the axis direction of the central pivot via the fourth shifting control unit, then to move the lighting capture module, and based on the feedback signal, makes the
    lighting capture module move on the sliding bar using the third shifting control unit till the whole image of the target area is obtained.

2. The automatic surgical lighting device as in claim 1, wherein the device further comprises:
    a mechanic arm that connects the supporting element and the central pivot and is situated between them; and
    at least one first shifting control unit that is set on the mechanic arm and is electronically connected to at least one control unit, the control unit, based on the feedback signal, moves the mechanic arm via the first shifting control unit in order to move the lighting capture module till the image of the whole target area is captured.

3. The automatic surgical lighting device as in claim 2, wherein the device further comprises a second shifting control unit that is set on the central pivot and the mechanic arm, the second shifting control unit is electronically connected to at least one control unit, the control unit, based on the feedback signal, rotates the central pivot on the axis of its conjuncture with the mechanic arm via the second shifting control in order to have the axis of the central pivot vertical to the target area.

4. The automatic surgical lighting device as in claim 1, wherein the control unit, based on the feedback signal, slides the lighting capture module on the sliding bar via the third shifting control unit till the whole image of the target area is obtained.

5. The automatic surgical lighting device as in claim 1, wherein the control unit, based on the feedback signal, makes the lighting capture module on the sliding bar rotate vertically to the axis direction of the sliding bar using the third shifting control unit till the whole image of the target area is obtained.

6. The automatic surgical lighting device as in claim 1, wherein the control unit, based on the feedback signal, makes the lighting capture module on the sliding bar rotate on the axis of the sliding bar till the whole image of the target area is obtained.

7. The automatic surgical lighting device as in claim 1, wherein the lighting capture module further comprises:
    an illuminating source that is set on the sliding bar via the third shifting control unit and lights the target area; and
    an image detector that is set on the sliding bar via the third shifting control unit and connects electronically to the control unit, the image detector capture constantly and periodically the image of the target area in order to send feedback signals.

8. The automatic surgical lighting device as in claim 1, wherein the lighting capture modules capture periodically the images to send feedback signals.

9. The automatic surgical lighting device as in claim 1, wherein the supporting element is a supporting set or a supporting frame attached to clinic chair.

10. The automatic surgical lighting device as in claim 1, wherein the control unit can be set exteriorly or be integrated in the lighting capture module or the supporting element.

11. The automatic surgical lighting device as in claim 1, wherein the target area can be a mouth cavity area, a detectable target object in an operation, the hand of the surgeon, a dental hand-piece, a dental mirror, the teeth or the shape of the mouth.

12. The automatic surgical lighting device as in claim 1 which further comprises:
- a mechanic arm that connects the supporting element and the moving element and is situated between them; and
- at least one first shifting control unit that is set on the mechanic arm and is electronically connected to at least one control unit, the control unit, based on the feedback signal, moves the mechanic arm via the first shifting control unit in order to move the lighting capture module till the image of the whole target area is captured.

13. The automatic surgical lighting device as in claim 1, wherein the control unit is preset with at least one target zone corresponding to at least one lighting capture module, the control unit receives the feedback signal, compares with the template image of the corresponding target zone and moves the lighting capture module via the moving element according to the result obtained in order to move the lighting capture module till the image is in the corresponding target zone and the image of the whole target area is captured.

\* \* \* \* \*